United States Patent [19]
Jackson

[11] Patent Number: 4,753,648
[45] Date of Patent: Jun. 28, 1988

[54] SANITARY NAPKIN ADHESIVELY ATTACHED VIA ELASTIC MEMBER

[75] Inventor: Wanda W. Jackson, Hightstown, N.J.

[73] Assignee: Personal Products Company, Milltown, N.J.

[21] Appl. No.: 47,093

[22] Filed: May 8, 1987

[51] Int. Cl.⁴ .......................................... A61F 13/16
[52] U.S. Cl. .................................. 604/389; 604/393
[58] Field of Search ............ 604/389, 390, 393, 387, 604/400, 401, 358, 385.1

[56] References Cited

U.S. PATENT DOCUMENTS

| | | | |
|---|---|---|---|
| 1,664,626 | 4/1928 | Ito | 604/400 X |
| 1,683,125 | 9/1928 | Brady et al. | 604/401 X |
| 2,742,903 | 4/1956 | Lightner | 604/387 |
| 3,227,160 | 1/1966 | Younger | 604/401 X |
| 4,072,151 | 2/1978 | Levine | 604/387 |

*Primary Examiner*—Stephen C. Pellegrino

[57] ABSTRACT

A sanitary napkin is disclosed for providing improved product fit and adjustability to different body sizes. The napkin provides for secure product placement during body movements and employs one or more elastic members attached to the ends of a central absorbent having a body fluid pervious surface and a body fluid impervious surface. The napkin also includes adhesive tabs attached to the end of said elastic members for re-attachment of the napkin after initial use.

18 Claims, 2 Drawing Sheets

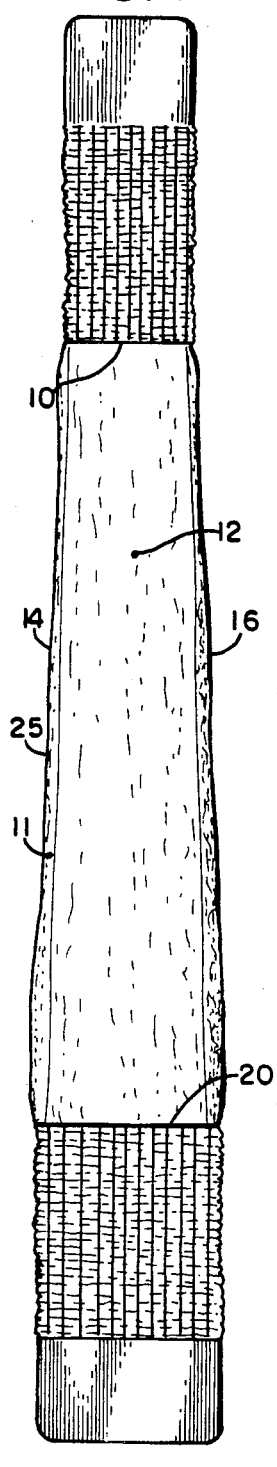
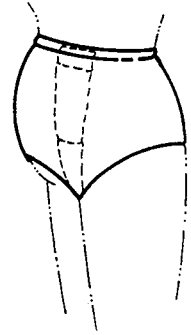
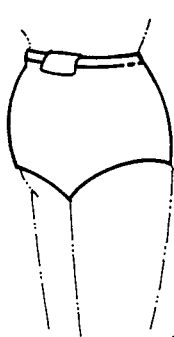
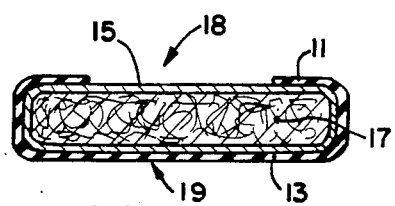

SANITARY NAPKIN ADHESIVELY ATTACHED VIA ELASTIC MEMBER

FIELD OF THE INVENTION

This invention relates to protective, absorbent liners for undergarments that exhibit improved product fit close to the body and in particular, to thin liners that are adjustable to different body sizes and provide secure product placement during body movements.

BACKGROUND OF THE INVENTION

Currently available sanitary napkins now teach a composite of materials generally comprising an absorbent core with a soft, liquid pervious surface facing the body and a fluid impervious surface facing the garment. The pervious and impervious surfaces may be commonly extended and heat sealed together to form short, sealed tabs to encapsulate the absorbent core. Adhesives are customarily applied to the garment facing side of the product for securing the napkin to clothing during use.

Adhesive systems for securing sanitary napkins to the garment must tenaciously adhere to the garment at all times. They must resist moisture, sudden torques generated by movements of the body and frictional shearing forces exerted by the movements of the various layers of clothing worn by the user.

External sanitary protection is known to greatly depend upon the proximity of the napkin to the perineal area. A close fit allows the napkin to collect fluid near the source of the exit from the body and minimizes fluid traveling along the body. However, despite the importance of fit to sanitary protection, prior art napkins adhesively secured to the crotch of the garment rely on the relatively loose fit of the user's undergarments. Panties worn while menstruating are often older, well-worn garments which fit poorly. New panties, unless specially designed to do so, rarely hold and maintain the napkin close enough to be effective. Even specially designed undergarments are deemed by many women to be binding and uncomfortable.

One prior art solution to the fitting problem has been to use sanitary belts to independently support the napkin. Napkins with long tab ends worn with sanitary belts achieve the necessary closeness to the body but are often uncomfortable, inconvenient to use, and cause an indiscreet appearance which women find objectionable. Moreover, belts suspend a napkin in such a way that it is allowed to shift and twist, greatly reducing its effectiveness.

Another solution, contemplated by the prior art, is to attach the product ends to the skin. Several patents have been directed to devices for collecting body fluids that employ adhesive attachments to the skin. Zamist, U.S. Pat. No. 3,906,952, is directed to an anatomically-contoured sanitary napkin having adhesive patches which attach to the skin of the wearer. These patches have non-disposable, die-cut grippers to receive the ends of the napkin. Levine, U.S. Pat. No. 4,072,151 describes a catamenial napkin having a long, full-sized napkin with non-irritating adhesive strips on its longitudinal ends for attaching to the body. Sohn, U.S. Pat. No. 4,484,919, teaches a rectal area dressing for anal incontinence. This rectoperineal device has pressure-sensitive adhesive on an elongated absorbent pad and on extending end members which adhere to the skin surfaces. While these inventions generally provide a close fit to the wearer's body, they do not permit stretching in the longitudinal direction to adjust to the wearer's individual sizing needs. Such devices, moreover, are not flexible enough to allow the pad to move with the body and return to its original position during stooping, bending and twisting. This can lead to uncomfortable binding and twisting of the napkin. Furthermore, the attachment sites of these products, being susceptible to sudden torques and shearing forces, are not always reliable in securing product placement.

Accordingly, there is still need for a napkin that provides a comfortable fit even during body movements while at the same time enabling adjustments for the wearer's size. There is also a need for a napkin that provides close placement against the wearer's body at all times, collecting fluid close to the source without wetting undergarments.

SUMMARY OF THE INVENTION

In accordance with the teaching of this invention, a sanitary napkin is provided with an adjustable length by discretionary extension of one or more elastic members. Additionally, the body is permitted to move in ways counter to the original positioning, since the elastic member will stretch and recover to automatically adjust to different body positions without binding or constricting. The adhesive tabs of this invention remain securely anchored to their attachment sites on the garment or on the skin as the strain is absorbed by the elastic members. The tabs may be provided with several layers or areas of adhesive to provide for repeated attachment and removal.

It is, therefore, an object of this invention to provide a sanitary napkin that is held close to the wearer's body, collecting fluid close to the source.

It is another object of this invention to provide a sanitary napkin with elastic members that permit adjustments to different body sizes.

It is still another object of this invention to provide a sanitary napkin that is self-adjusting to body position without binding.

It is still another object of this invention to provide a sanitary napkin that remains securely attached to the body during body motion.

With these and other objects in view, which will become apparent to one skilled in the art as the description proceeds, this invention resides in the novel construction, combination, arrangement of parts and methods substantially as hereinafter described and more particularly defined by the attached claims.

BRIEF DESCRIPTION OF THE DRAWINGS

The accompanying drawings illustrate a complete embodiment of the invention according to the best mode so far devised for the practical application of the principles thereof, and in which:

FIG. 1: is a front elevation of the sanitary napkin of this invention illustrating a planar view of the body-facing side of the napkin;

FIG. 2: is a rear elevation of the garment facing side of the napkin showing release papers 22 and 24 partially peeled from the adhesive tabs 26 and 28;

FIG. 3: is a perspective view from the front of a wearer indicating how the napkin is attached to the skin;

FIGS. 4 (a) and (b): are perspective views from the back of a wearer indicating how the napkin can be attached to an undergarment;

FIG. 8: is an enlarged detail of a transverse cross-sectional view of the napkin of FIG. 2, taken through line 8—8.

DETAILED DESCRIPTION OF THE INVENTION

Figure 5:
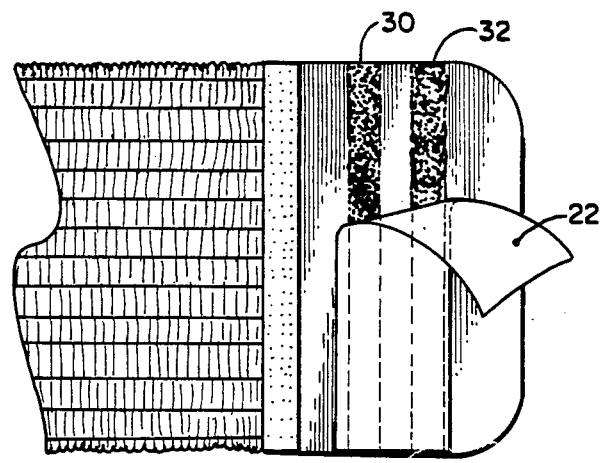
FIG. 5: is an enlarged detail of tab 28 in FIG. 2 illustrating the planar view including a peel-back view of the adhesive strips 30 and 32.
Figure 6:
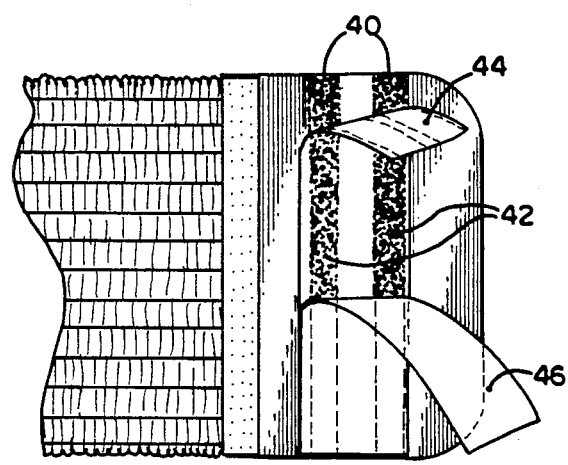
FIG. 6: is an enlarged detail illustrated with a peel-back view of an alternative tab embodiment having multiple layers of adhesive 40 and 42 separated by multiple release papers 44 and 46.
Figure 7:
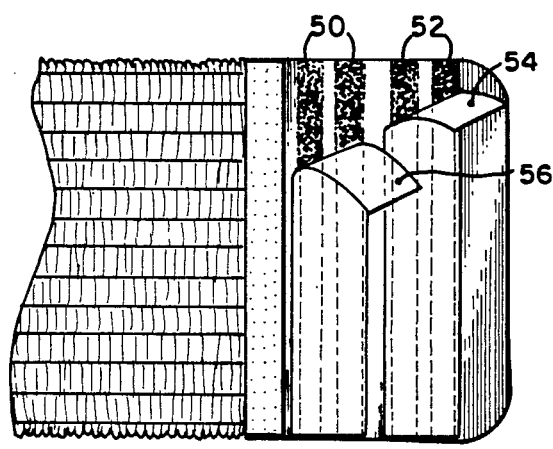
FIG. 7: is an enlarged detail illustrated with a peel-back view of an alternative tab embodiment having multiple adhesive surfaces 50 and 52 having separate release papers 54 and 56.

FIGS. 1-4 and 8 illustrate, in front and rear planar, in perspective, and transverse cross-section, a sanitary napkin 25 embodying the teachings of this invention. The napkin 25 comprises a central absorbent 12 having longitudinally extending edges 14 and 16, a body facing, body fluid pervious side 18, and a garment facing, body fluid impervious side 19. At least one elastic member is attached to one of the transverse ends of the napkin which provides the user with size adjustment capability and prevents binding of the napkin during body motions such as bending or twisting. Adhesive tabs 26 and 28 are provided for attaching the napkin 25 to the skin or to the undergarment. It will be clear that many different adhesive configurations will become apparent to those skilled in the art. However, this invention teaches preferred configurations as illustrated in FIGS. 5-7, including those that permit re-attachment to the skin or undergarment such as multiple adhesive surfaces 50 and 52 having releasable coverings 54 and 56 illustrated in FIG. 7.

The choice of materials for use in the napkin of this invention may be any of the well known absorbent and superabsorbent materials utilized in the art of manufacturing these products. The central absorbent 12 of this invention should be made of soft, comfortable material. Adequate absorbency may be built into the core of the absorbent without adding bulk by adding super absorbent materials, now known, which have the properties of high-liquid retention, e.g., cross-linked acrylate polymers. The absorbent should retain fluid well without allowing it to squeeze out and re-wet the wearer. Generally, the central absorbent 12 should be about 5-20 inches in length, preferably 10-14 inches and most preferably about 11-13 inches. In the preferred embodiment, the central absorbent 15 is tapered from about 2.75 to 5 inches, preferably about 3 inches, at one transverse end to about 0.5 to 2.5 inches, preferably about 2 inches, at the other transverse end. The widest portion of the napkin 25 is usually worn in the front of the wearer, however, the front and the back may be reversed at the wearer's discretion.

The materials used in fabricating the core 17 of the central absorbent 12 preferably comprise loosely associated absorbent hydrophilic materials such as cellulose fibers, wood pulp, regenerated cellulose or cotton fibers, and others generally known in the art. Such fibers may be chemically or physically modified and the core may include such fibers in combination with other materials, both natural and synthetic, such as hydrophilic foams, hydrophilic polymers or the like. For the preferred embodiment of this invention, wood pulp is the material of choice because of its availability and inexpensive cost. In the most preferred embodiment of this invention, ground wood pulp is combined with polyacrylate-super absorbent tissue positioned between the wood pulp and a moisture impervious backing.

Covering the side of the napkin to be worn against the body of the user, herein referred to as the body facing side 18, is a body fluid pervious surface 15. This surface 15 may be any woven or non-woven material pervious to body fluid contacting its surface. The body facing material should be soft and easily permeated by body fluids. Preferably, it would be a material which allows the passage of fluid into the napkin without appreciable wicking in the horizontal plane. Furthermore, it should retain little or no fluid in its structure to provide a relatively dry surface next to the skin. Generally, the fluid permeable surface 15 is a single, rectangular sheet of material having a width sufficient to cover the body facing side 18 or the core of the central absorbent 17. Preferably the fluid pervious surface 15 is longer than the core 17 so as to form end tabs 21 and 23, which may be sealed to fully enclose the core 17. The fluid pervious surface 15 is generally made of well-known cellulosic material such as cotton or rayon treated to be hydrophobic. Preferably, the body fluid pervious surface 15 comprises fibers or filaments of thermoplastic hydrophobic polymers such as polyethylene or polypropylene. In one preferred embodiment of this invention, the pervious surface comprises a bicomponent fiber comprising a polyester core covered by a polyethylene sheath.

The sanitary napkin of this invention further includes a body fluid barrier surface 13 on the garment facing side of the central absorbent 12. The impervious surface 13 should be made from fluid impermeable material such as polyethylene or a non-woven material coated with an impermeable film. The impervious surface preferably allows the passage of air and moisture vapor while substantially blocking the passage of fluid to the outer surface. The impervious surface 13 in the preferred embodiment is sealed together with the pervious surface 15 around the perimeter of the central absorbent 12 to form a "boat", as depicted in FIG. 8, to prevent leakage of fluid from the sides of the central absorbent.

The impervious surface 13 may be heat sealed or fastened by way of adhesives to the core 17 or to the core 17 wrapped in a fluid pervious surface cover. In a preferred embodiment, the overlapped portion of the impervious surface 11. in FIGS. 1 and 8, forms a "window" of pervious material on the body side surface of the napkin 25. It is expected that those skilled in the art will find variations of this concept readily apparent. The impervious surface 13 may comprise any thin, flexible, body fluid impermeable material material as, for example, a polymeric film, e.g., polyethylene, polypropylene, cellophane or even a normally fluid pervious material that has been treated to be impervious to liquids while permitting the passage of air and moisture vapor such as fluid repellent paper or fabric. The fluid impervious layer 13 is generally fastened to the central absorbent 12 by means of a plurality of longitudinally extending lines of adhesive. Preferably, however, the impervious surface 13 is a heat bondable material such as polyethylene which can be bonded to the pervious surface 15 to completely enclose the core 17 of the central absorbent 12. In one embodiment of this invention, the impervious surface 13 is fabricated using 1.0 mil microporous polyethylene.

An important and novel element of this invention is the addition of at least one elastic member attached to one of the transverse ends of the central absorbent 12. It is envisioned that elastic materials can be added to both ends of the central absorbent to provide more flexibility in use. These stretchable ends preferably are contained within a soft, fabric-like material for non-irritating contact with the skin. The ends should be extendable by at least 25%, preferably by at least 50%, and most preferably by 100%. Extensions made in the longitudinal direction allow the wearer to stretch the product to whatever length provides the best fit for that individual. Moreover by extending the napkin, the adhesive ends may be placed well clear of hair or sensitive areas. Elastic members 27 and 29 can be the same width as the transverse ends 10 and 20 of the central absorbent 12 or may be wider or narrower relative to these ends. The elastic members are generally about 1 to 6 inches long, preferably about 2 to 5 inches, and most preferably about 3 to 4 inches. In one preferred embodiment of this invention, the elastic members 27 and 29 are fabricated using two layers of non-woven polypropylene with integral rubber monofillaments sandwiched between the layers.

The adhesive tabs 26 and 28, when located on the body facing side of the napkin for attachment to the skin, can be made of any known, non-irritating, hypoallergenic adhesive fastened to a fairly stable substrate. See Ballath, U.S. Pat. No. 4,335,026, which discloses non-irritating adhesive formulations, and is hereby incorporated by reference. Preferable adhesive compositions for attachment to the skin include those containing an elastomeric blend of a selected rubber olefin terpolymer, plasticizer, reinforcing filler, tackifier and stablizer. One adhesive embodiment anticipated by applicant includes a mixture containing 34.2% by weight polyisoprene, 10.8% by weight ethylene-propylene-hexadiene terpolymer, 10.1% by weight isomeric liquid polybutene and 44.9% by weight solid tackifier. Applicant also anticipates using a water based acrylic adhesive emulsion having a high shear and low peel resistance. When attachment to the garment is the preferred embodiment, adhesive compositions may be any of the already known pressure-sensitive compositions suitable for sanitary napkins including, for example, the waterbased pressure-sensitive adhesives such as the acrylate adhesives, e.g., vinyl acetate-2 ethyl hexyl acetate copolymer which is generally combined with tackifiers such as, for example, ethylene amine. Alternatively, the adhesive may comprise a rapid setting thermoplastic (hot melt) adhesive. The adhesive elements may also comprise a two-sided adhesive tape.

Layers of adhesive 40 and 42 may be provided as in FIG. 6, with release papers 44 and 46 to allow for reattachment. Another preferred embodiment, FIG. 7, includes a tab in which only a portion of the adhesives 50 and 52 are exposed at any given time allowing other portions to be exposed as needed for repeated attachment. As shown in FIG. 5, the adhesive may be in the form of two longitudinally extending bands. However, it will be understood by those skilled in the art that many variations in the number and shape of these adhesive elements are possible.

Release paper 22 in FIG. 5 is generally provided to protect the adhesive tabs prior to use. The release paper 22 may be made of any suitable sheet-like material which adheres with sufficient tenacity to the adhesive tabs 28 and 26 to remain in place, but which can be readily removed when the napkin 25 is to be used. A particularly useful material is a semi-bleached kraft paper, the adhesive contacting side of which has been silicone coated to provide easy removal from the adhesive just prior to use.

FIGS. 1 and 2 show a representation of a preferred construction of this invention. The central absorbent 12 in this embodiment is 12 inches long, three inches wide at one end tapering to two inches wide at the other end. The body fluid pervious and impervious surfaces 15 and 13 are sealed together around the perimeter of the pad and the impervious material is then folded over onto the central absorbent to form a boat to prevent leakage of fluid from the sides. The elastic members 27 and 29 are rectangular and are either narrower or equal in width to the central absorbent 12 on each product end. These members are both 3 to 4 inches long in the relaxed state and are capable of stretching to a maximum of 8 inches in this embodiment. Adhesive tabs 28 and 26 are attached along the edges of each elastic member and are also the same width as the transverse ends 10 and 20 of the central absorbent 12. In accordance with the teachings of this invention, the pervious and impervious surfaces 15 and 13 extend longitudinally beyond the transverse edges 10 and 20 of the central absorbent 12, and are joined to form elongated tabs 21 and 23 which extend beyond the transverse edges 10 and 20.

Referring now to FIGS. 5 through 7, there are illustrated various preferred embodiments for the adhesive tabs of this invention. Shown in FIG. 5 is an enlarged detail of tab 22 in FIG. 2 illustrating the planar view including a peel-back view of the adhesive strips 30 and 32. In this embodiment, the user merely peels the release papers from the adhesive areas and applies the napkin to the skin or garment as depicted in FIGS. 3 and 4(a) and (b). It should be noted that the adhesive can be applied to either side of tabs 26 and 28 to enable attachment to the skin, as in FIG. 3, or to the garment, as in FIGS. 4(a) and (b). When attachment to the garment is preferred, the tabs can be fastened to the inside of the garment as in FIG. 4(a), or folded over the waist band to the outside of the panty as in FIG. 4(b).

FIG. 7 is an enlarged detail and illustrated with a peel-back view of an alternative tab embodiment having multiple adhesive surfaces 50 and 52 having separate release papers 54 and 56. This embodiment has the advantage of permitting re-attachment of the napkin to permit adjustment by the wearer after the initial application. Alternatively, re-attachment is also permitted using multiple layers of adhesive 40 and 42 separated by release paper 44 as indicated in FIG. 6.

From the foregoing it can be realized that this invention provides an improved sanitary napkin. The advantages over the prior art are: improved product fit closer to the body, adjustability to different body sizes, self-adjustability to body position, and secure product placement. Although various embodiments have been illustrated, this was for the purpose of describing, but not limiting, the invention. Various modifications, which will become apparent to one skilled in the art, are within the scope of this invention described in the attached claims.

What is claimed is:

1. An sanitary napkin for adhesively attaching to skin or undergarment comprising:
   (a) a central absorbent having longitudinally extending edges, a body facing side, an undergarment facing side, and transverse ends;

(b) a body fluid pervious surface on said body facing side;

(c) a body fluid impervious surface on said undergarment facing side;

(d) at least one elastic member attached to one of said transverse ends having a free end;

(e) a first adhesive tab disposed on said free end of said elastic member for attaching said napkin to the skin; and (f) a second adhesive tab attached to the other one of said transverse ends for attaching said napkin to the skin.

2. The sanitary napkin of claim 1 wherein said impervious surface is polyethylene.

3. The sanitary napkin of claim 1 wherein said impervious surface is a non-woven material coated with an impermeable film.

4. The sanitary napkin of claim 1 wherein said elastic member comprises a non-absorbent material.

5. The sanitary napkin of claim 1 wherein said central absorbent is about 5–20 inches in length.

6. The sanitary napkin of claim 1 wherein said central absorbent is about 10–14 inches in length.

7. The sanitary napkin of claim 1 wherein said central absorbent comprises a progressively decreasing width from one of said transverse ends to the other one of said transverse ends.

8. The sanitary napkin of claim 1 comprising a second elastic means disposed between said second adhesive tab and said other one of said transverse ends.

9. The sanitary napkin of claim 1 wherein said first and second adhesive tabs are disposed on a garment facing side of said napkin, said adhesive tabs being capable of folding over the waistband of said garment to contact the skin.

10. The sanitary napkin of claim 1 wherein said first and second adhesive tabs are disposed on a body facing side of said napkin.

11. The sanitary napkin of claim 1 wherein said elastic member is covered in fabric.

12. The sanitary napkin of claim 1 wherein said elastic member is covered in fabric on its body facing side.

13. The sanitary napkin of claim 1 wherein said elastic member is longitudinally extendable by at least 25%.

14. The sanitary napkin of claim 1 wherein said elastic member is longitudinally extendable by at least 50%.

15. The sanitary napkin of claim 1 wherein said elastic member is longitudinally extendable by at least 100%.

16. The sanitary napkin of claim 1 wherein said elastic member is narrower than said transverse end.

17. The sanitary napkin of claim 1 wherein said adhesive tabs comprise a plurality of adhesive surfaces having releasable coverings to allow for re-attachment of said tabs.

18. The sanitary napkin of claim 1 wherein said adhesive tabs comprise a plurality of adhesive layers, said layers being separated by releasable coverings to allow for re-attachment of said tabs.

* * * * *